United States Patent [19]

Sump

[11] Patent Number: 4,570,271
[45] Date of Patent: Feb. 18, 1986

[54] POROUS COATINGS FROM WIRE MESH FOR BONE IMPLANTS

[75] Inventor: Kenneth R. Sump, Richland, Wash.

[73] Assignee: Battelle Development Corporation, Columbus, Ohio

[21] Appl. No.: 561,577

[22] Filed: Dec. 14, 1983

Related U.S. Application Data

[63] Continuation-in-part of Ser. No. 287,431, Jul. 27, 1981, abandoned.

[51] Int. Cl.$^4$ ............................................... A61F 1/24
[52] U.S. Cl. .................................... 623/18; 228/173.5; 228/193
[58] Field of Search .................... 228/178, 173 F, 182, 228/193; 3/1.91, 1.913

[56] References Cited

U.S. PATENT DOCUMENTS

| | | | |
|---|---|---|---|
| 3,789,498 | 2/1974 | Cole | 228/193 |
| 4,038,703 | 8/1977 | Bokros | 3/1.91 |
| 4,064,567 | 12/1977 | Burstein et al. | 3/1.91 |
| 4,088,258 | 5/1978 | Regalbuto | 228/193 |
| 4,245,769 | 1/1981 | Meginnis | 228/193 |
| 4,252,263 | 2/1981 | Houston | 228/193 |
| 4,261,063 | 4/1981 | Blanquaert | 3/1.91 |
| 4,315,591 | 2/1982 | Houston | 228/193 |
| 4,365,356 | 12/1982 | Broemer et al. | 3/1.91 |
| 4,365,357 | 12/1982 | Draenert | 3/1.91 |

FOREIGN PATENT DOCUMENTS 2029749  3/1980  United Kingdom ................ 228/193

Primary Examiner—Nicholas P. Godici
Assistant Examiner—M. Jordan
Attorney, Agent, or Firm—Wells, St. John & Roberts

[57] ABSTRACT

A method of coating areas of bone implant elements and the resulting implant having a porous coating are described. Preselected surface areas are covered by a preform made from continuous woven lengths of wire. The preform is compressed and heated to assure that diffusion bonding occurs between the wire surfaces and between the surface boundaries of the implant element and the wire surfaces in contact with it. Porosity is achieved by control of the resulting voids between the bonded wire portions.

9 Claims, 3 Drawing Figures

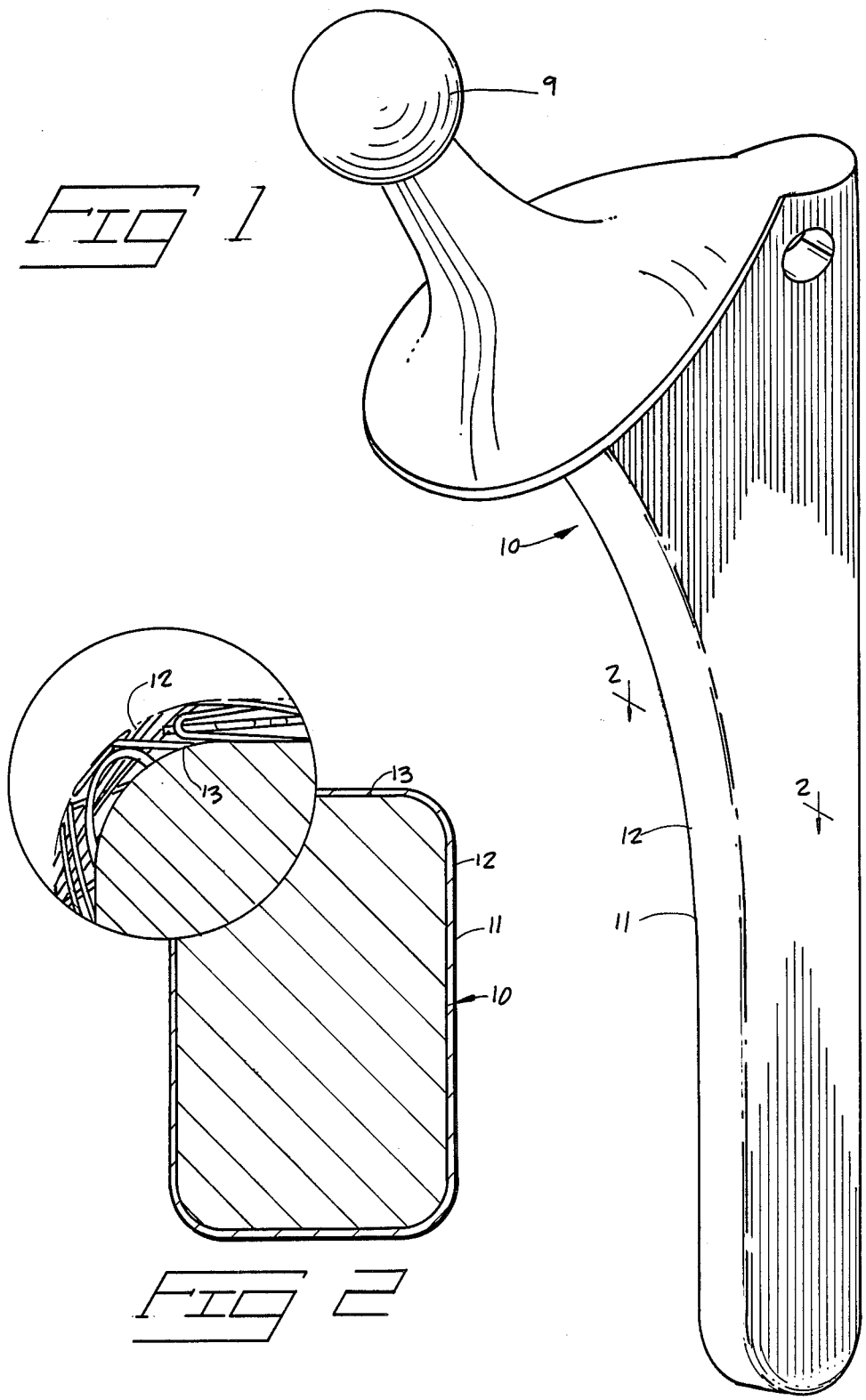

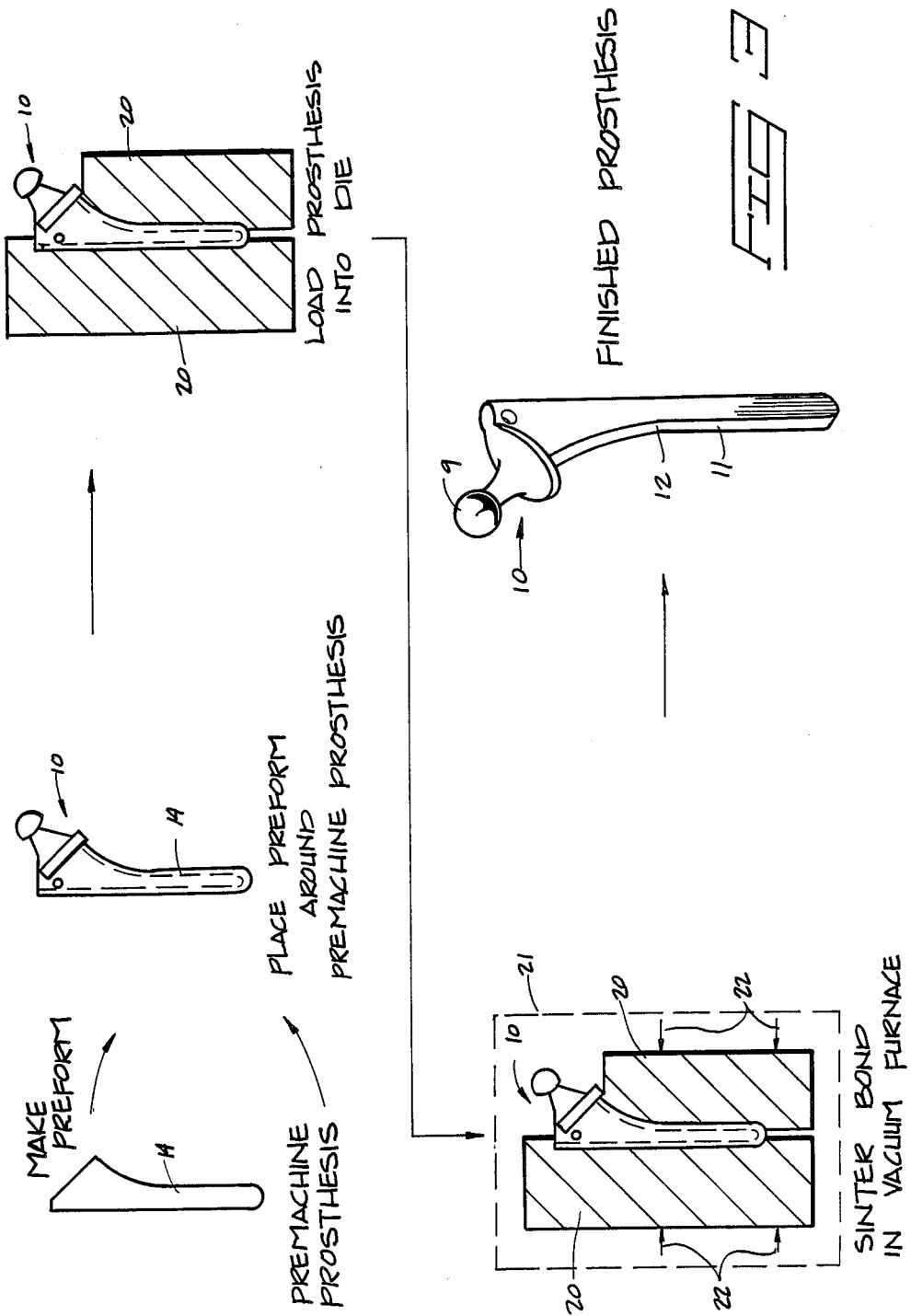

POROUS COATINGS FROM WIRE MESH FOR BONE IMPLANTS

RELATED APPLICATIONS

This is a continuation-in-part of application Ser. No. 287,431, filed July 27, 1981, now abandoned.

TECHNICAL FIELD

This disclosure relates to the production of a porous coating about preselected metallic surface areas on bone implant elements for subsequent tissue ingrowth applications. The coating is produced by compressing a preformed metallic cover of continuous wire mesh over the implant surfaces to be coated. It requires adequate application of heat and pressure about the cover to assure sintering of the wires to one another and to the adjacent surface areas. The resulting porous coating has interconnected pores through which hard or soft body tissues can grow to attach the bone implant element to bone.

BACKGROUND ART

U.S. Pat. No. 3,852,045 to Wheeler, Sump, and Karagianes discloses a porous metallic material including a network of interconnected voids or pores. It is formed on a surgical prosthetic device for tissue ingrowth purposes. The voids or pores about the resulting surface areas are produced in the coating material by use of a composite material including expendable void formers. The described composite material is treated by high energy rate forming pressures to densify its structure prior to removal of the expendable void former. Substantial thicknesses of the void coating on substrate metallic elements is disclosed.

While the products resulting from the systems taught in U.S. Pat. No. 3,852,045 have performed satisfactorily, the practical application of the system is severely limited by both the expense and availability of equipment for the required high energy rate forming steps. Furthermore, such steps are of questionable value when attempting to produce a relatively thin porous coating on implant elements, since the high pressures to which the elements would be subjected might result in structural damage to them.

U.S. Pat. No. 3,986,550 to Restaker et al describes prosthetic devices having porous sections. It discusses prior efforts to use consolidated metal powders to produce porous metals for this purpose, but dismisses them as being brittle and having unacceptable toughness. The patent specifically describes a process for producing a porous section by use of short fiber strands. The strands are molded and sintered to interconnect the metal fibers. It states that by repressing procedures, external dimensions of the coated prosthesis can be precisely regulated to the excavation in the receiving bone so that a zero clearance fit is achieved. It describes that long wire lengths give more interlock and better molded strengths, but notes that the longer the wire, the more difficult it is to feed into dies. No mention is made of preforming the wires or using wire mesh of any type.

An article published in the *Journal of Bone and Joint Surgery*, Volume 53-A, No. 1, January, 1971, Pages 101 through 114, titled "Sintered Fiber Metal Deposits as a Basis for Attachment of Implants to Bone", by Galante et al, also describes the molding and sintering of short metal fibers for production of implant materials. It contains a review of available literature publications relating to porous elements of this type, including open pore materials derived from powders consolidated and shaped in molding dies under pressure. The article discloses coating of cylinders by pressing fiber sleeves to form them separately, but the sleeves discussed are produced from individual kinked lengths of wires. This would appear to expose fiber ends at the resulting coated surface and would produce a surface that would include discontinuities and lack desired uniformity. Also, individual fibers pressed in a random mat would not result in a coating having uniform porosity or strength.

According to the present invention, relatively thin porous metallic coatings are produced about selected surface area configurations on a bone implant element by performing a sleeve or surface covering from a wire mesh produced from continuous lengths of wire. The mesh is preferably knitted, braided, wound or woven in some manner to produce a uniform mesh structure which, when pressed, will have relatively uniform porosity in the resulting voids that are formed between the wires. The wires are made from a material either identical to or metallurgically compatible with the metallic surface being coated. They are heated and pressed in place about the surface to effect diffusion bonding between engaged wire sections as well as between the surface area and the wire surfaces in contact with it.

DISCLOSURE OF INVENTION

The present method for producing a porous coating on a preselected metallic surface area of a bone implant element for tissue ingrowth applications comprises the step of first overlaying the area with a multi-layer covering comprising a continuous metallic wire mesh. The covering is compressed against the preselected surface area. Compression is required during the heating step, and can be accomplished prior to heating as well. The preselected surface area and covering are then heated to maintain an elevated temperature at which diffusion bonding occurs in the materials. The resulting coating will have a surface configuration complementary to the mold in which it is compressed. Controlled porosity throughout the coating results from the uniform spacing between the wires in the initial preform. The degree of compression will control the ultimate amount of porosity in the final coating.

It is an object of this disclosure to achieve controlled pore size and morphology in a porous coating without requiring the use of high energy rate forming pressures.

Another object is to provide porosity in the coating sufficient for tissue ingrowth applications, while retaining adequate strength properties for practical use in surgery.

Another object of this invention is to provide a practical thin porous coating on metallic bone implant surfaces which can retain complex surface configurations desired about the surfaces.

Finally, an object of the invention is to develop a practical process using presently available techniques, equipment and raw materials.

DESCRIPTION OF THE DRAWINGS

A preferred and alternate embodiment of this invention is illustrated in the accompanying drawings, in which:

FIG. 1 is a perspective view of an implant element having porous coated surfaces.

FIG. 2 is an enlarged fragmentary transverse sectional view taken substantially along line 2—2 in FIG. 1 with a circled corner area further enlarged for illustration; and FIG. 3 is an illustrative flow diagram illustrating the steps of the present process.

BEST MODE FOR CARRYING OUT THE INVENTION

In compliance with the constitutional purpose of the Patent Laws "to promote the progress of science and useful arts" (Article 1, Section 8), applicant submits the following disclosure of the invention.

FIGS. 1 and 2 generally illustrate a known configuration of a hip prosthesis 10. The prosthesis 10, which is a relatively common bone implant element used in surgical repair of hip joints, includes an elongated shank 11 intended to be inserted axially within a supporting bone structure. It is capped by a ball structure generally shown at 9. In most surgical installations of such a prosthesis, the shank 11 is anchored to the bone structure by adhesives.

As illustrated in FIGS. 1 and 2, the outer surfaces of the shank 11 are covered by a porous metallic coating 12 that surrounds an inner solid metal substrate 13. The coating 12 is bonded to the substrate 13, and includes interconnected pores through which soft and hard living tissues can grow after implantation of the prosthesis 10.

The present process is initiated by cleaning and machining of the preselected metallic surface areas upon which the coating is to be formed. Additionally, a preform covering of continuous woven wire complementary to the surfaces is produced by conventional multi-layer knitting, braiding, winding, weaving or other continuous wire processes. The preform covering is generally shown in FIG. 3 at 14. It is formed to complement the geometry of the surfaces to be covered by it. Its initial thickness will be governed by the desired final thickness of the coating and degree of compression to which it is to be subjected in order to produce the required final coating porosity.

The preform covering 14 can be in the form of a sleeve, a complete cover, or a curved or flat pad shaped to overlie the surfaces involved. It should be produced from wires made of metallic material matching or compatible with the surface area being coated.

There are three alternatives available for effecting the required compression and diffusion bonding of preform covering 14. It can be subjected to cold compression followed by heating in locked dies. It can be subjected to cold compression followed by hot compression. It can also be subjected to hot compression alone. In each instance, diffusion bonding is achieved by application of heat while the wires in the preform are under pressure. Bonding of all areas of contact of the wires is a result of active pressing, retention in compressed locked dies, thermal expansion forces within confining dies, or a combination of such factors.

The first step in utilizing this process is to place the preform covering 14 about the areas on prosthesis 10 which are to be coated. This can be accomplished externally from any die system, or the preform covering 14 can be first placed within a die and the prosthesis 10 subsequently inserted within it. In either case, the preform covering 14 and prosthesis 10 are eventually loaded into a compression mold or die and subjected to compressive forces capable of accurately deforming the surface areas under controlled conditions prior to and during subsequent heating to achieve reproducible coatings on the manufactured bone implant elements or prosthesis. The selected compression system must be capable of accurately forming required complex surface areas typically required in prosthetic implants such as that illustrated in the drawings. While isostatic pressing might be used, the specific illustration shown in FIG. 3 shows use of mechanical dies having two or more segments for compression of the coating surface areas.

The preform covering 14 and prosthesis 10 are placed within the complementary jaws 20 of a pressing die, with the die cavity surfaces overlying the preselected surface areas of the prosthesis to be coated. Initial pressing is preferably accomplished without heating to compact the volume of the initially loose covering material. Such initial pressing in a die may eliminate the need for high temperature pressing devices. The compessed die might then be mechanically locked prior to loading it into a furnace for heating. This would maintain preform covering 14 under compression. The die jaws 20 and prosthesis are then subjected to heat within a furnace 21. The degree of compression might be increased or decreased as a result of heating, dependent upon the thermal coefficients of the materials in the prosthesis, the preform and the jaws 20 of the die.

Furnace 21 is preferably a vacuum furnace, since subjecting the preform 14 and prosthesis 10 to vacuum pressure during the heating step inhibits oxidation of the metallic alloys. Oxidation can also be minimized or prevented by heating the pressing die within a suitable inert atmosphere. The temperature of the prosthesis and preform must be raised to a level at which diffusion bonding between the prosthesis surface areas and the wires in contact with them and also between adjacent wire surfaces will be achieved at the compressive forces to which they are subjected. In the case of prosthetic surfaces and wire coatings made from Ti6A14V alloy, the temperature will be between 800° to 1400° C.

The prosthesis and covering wires might be simultaneously subjected to the application of pressure and heat within vacuum furnace 21 by movement of the jaws 20 as indicated by arrows 22. Compression of preform 14 will reduce the volume of the cover about the prosthesis surfaces to the desired coating thickness, which can be calculated with respect to wire size and density to achieve the resulting desired degree of porosity.

The process is completed by removing the prosthesis 10 from the pressing die. It should require no surface finishing. The resulting surface will be uniform throughout its area and will not include projecting wire ends or discontinuities. The use of continuous wire structures in the coating lends superior strength to the resulting coating beyond that which can be achieved by sintering of shorter wire lengths.

In an experiment designed to demonstrate that a knitted wire sleeve could be gravity sintered over a core in a compressed condition, a knitted tubular sleeve of Monel was sinter bonded over a nickel core in a vacuum furnace at 1,000° C. for two hours. The sleeve was knitted from 0.0045 inch diameter wire. The compressed sample had an outside diameter of 0.560 inches and an inside diameter of 0.480 inches. Monel and nickel materials were used in this experiment because of immediate availability, but the process is readily applicable to alloys typically used in prosthesis devices.

The knitted sleeve was inserted into an aluminum oxide tube and the nickel core then driven into the center of the sleeve. This caused compression of the knitted wire sleeve. The sinter bonding was designed to sinter to the wires to themselves at each contact point and also to sinter the wire surfaces to the core surfaces where they will contact.

The sample held its compressed shape when removed from the aluminum oxide tube. It did demonstrate the feasibility of the sintering step, although greater comressive force appears to be required for strength purposes. The porous metal density was about 20% of the total volume, but could be designed to be much greater.

In applying the method to a prosthetic surface, unalloyed titanium or Ti6A14V alloys will typically be used. Wires of these materials matching the substrate will be applied to the desired areas of the prosthesis by inserting a woven wire preform over the device. The wire preform will then be sintered bonded in place both to itself and to the device. During sinter bonding, the wire preform will be compressed. All porosity would be open porosity, with the size and shape being variable and within limits imposed by the weaving or knitting capability of the process used in production of the preform.

The compression of the preform during the sintering process, following assembly about the prosthesis, increases the coating density and promotes more bonding points. It is estimated that the compressed density will be between 15% to 50% of theoretical in the coating, using wire sizes between 100 to 200 microns in diameter.

An advantage of using a preformed coating made from wire is that this permits use of a wrought product rather than a powder, as has been previously attempted. There is no expendable phase material to remove in order to achieve the required porosity and no chance of contamination of the coating by other materials. The process appears to be very economical. It permits subassembly of the prosthesis outside a die or mold when desired. The processing steps appear to be limited to a minimum number for comparable systems.

In compliance with the statute, the invention has been described in language more or less specific as to structural features. It is to be understood, however, that the invention is not limited to the specific features shown, since the means and construction herein disclosed comprise a preferred form of putting the invention into effect. The invention is, therefore, claimed in any of its forms or modifications within the proper scope of the appended claims, appropriately interpreted in accordance with the doctrine of equivalents.

I claim:

1. A bone implant element for tissue ingrowth applications having a porous matrix coating directly bonded to a preselected metallic surface area thereof, the coating having interconnected pores through which soft and hard living tissues can grow after implantation of the bone implant element;

the coating being produced by the following steps:
overlaying the preselected surface area with a preform covering formed of a plurality of layers of continuous metallic wire mesh made from a material compatible with the material of the surface area and having a total material thickness equal to a desired preform coating thickness;
compressing the covering against the preselected surface area by subjecting it to compressive forces capable of accurately deforming the surface areas of the covering to the desired coating thickness to achieve a reproducible porous coating; and
heating the compressed covering while under pressure to an elevated temperature at which diffusion bonding occurs between all areas of contact between the wires in the wire mesh and also between the surface area and all areas of contact of the wires that engage it.

2. A method for producing a porous matrix coating directly bonded about a preselected metallic surface area of a bone implant element for tissue ingrowth applications, comprising the following steps:
overlaying the preselected surface area with a preform covering formed of a plurality of layers of continuous metallic wire mesh made from a material compatible with the material of the surface area and having a total material thickness equal to a desired preform coating thickness;
compressing the covering against the preselected surface area by subjecting it to compressive forces capable of accurately deforming the surface areas of the covering to the desired coating thickness to achieve a reproducible porous coating; and
heating the compressed covering while under pressure to an elevated temperature at which diffusion bonding occurs between all areas of contact between the wires in the wire mesh and also between the surface area and all areas of contact of the wires that engage it to produce a porous coating having interconnected pores through which soft and hard living tissues can grow after implantation of the bone implant element.

3. A method as set out in claim 2 wherein the preform covering is first compressed and molded to a shape complementary to the preselected surface area prior to the overlaying step.

4. A method as set out in claim 3 wherein the preform covering is compressed and molded to a density that is approximately 15% to 50% of its theoretical solid density and the wire diameter size is 100 to 200 microns.

5. A method as set out in claim 2 further comprising the step of producing the preform covering by continuous woven wire processes.

6. A method as set out in claim 3 further comprising the step of producing the preform covering by knitting continuous wires.

7. A method as set out in claim 2 further comprising the step of producing the preform covering by braiding continuous wires.

8. A method as set out in claim 2 further comprising the step of producing the preform covering by winding of continuous wires.

9. A method as set out in claim 2 wherein the preform covering is initially compressed prior to the heating step and is held under pressure in a loaded die during the heating step.

* * * * *